US010176277B2

(12) United States Patent
Cheng et al.

(10) Patent No.: US 10,176,277 B2
(45) Date of Patent: Jan. 8, 2019

(54) METHODS FOR THE ANALYSIS OF DISSOCIATION MELT CURVE DATA

(71) Applicant: LIFE TECHNOLOGIES CORPORATION, Carlsbad, CA (US)

(72) Inventors: Francis T. Cheng, Palo Alto, CA (US); Casey R. McFarland, San Francisco, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 832 days.

(21) Appl. No.: 14/011,190

(22) Filed: Aug. 27, 2013

(65) Prior Publication Data

US 2014/0067345 A1     Mar. 6, 2014

Related U.S. Application Data

(63) Continuation of application No. 12/359,241, filed on Jan. 23, 2009, now Pat. No. 8,538,733.
(Continued)

(51) Int. Cl.
*G01K 15/00*     (2006.01)
*G01K 19/00*     (2006.01)
(Continued)

(52) U.S. Cl.
CPC ....... *G06F 17/5009* (2013.01); *C12Q 1/6816* (2013.01); *G06F 19/18* (2013.01)

(58) Field of Classification Search
CPC ....... C12C 1/6816; G06F 19/18; G06F 19/10; G06F 19/12; G06F 19/14; G06F 19/16; G06F 19/20; G06F 19/24; C12Q 1/6816
(Continued)

(56) References Cited

U.S. PATENT DOCUMENTS 5,635,352 A * 6/1997 Urdea .................. C12Q 1/6813
                                                              435/6.1
6,051,380 A * 4/2000 Sosnowski ........... B01J 19/0046
                                                             257/E21.43
(Continued)

FOREIGN PATENT DOCUMENTS

WO     2001/053822     7/2001
WO     2001/53822     7/2001
(Continued)

OTHER PUBLICATIONS

Roche Diagnostics GmbH, LightCycler 480 Instrument—Software Version 1.4. 2008.*
(Continued)

*Primary Examiner* — An Do
(74) *Attorney, Agent, or Firm* — Jones Robb, PLLC

(57) ABSTRACT

Methods are provided that operate on raw dissociation data and dissociation curves to generate calibrations of the detected data and to further improve analysis of the data. The data can be taken from each support region of a multi-region platform, for example, from each well of a multi-well plate. Each support region can be loaded with portions of the same sample. In some embodiments, a dissociation curve correction can be calibrated for the sample, prior to a run of an experiment using such sample. In some embodiments, a method is provided for generating a melting transition region of dissociation curves that show the melting characteristics of the sample. In some embodiments, dye temperature dependence correction can be performed on the dissociation curve data to further improve analysis. In some embodiments, a feature vector can be derived from the melt data, and the feature vector can be used to further improve genotyping analysis of the dissociation curves.

18 Claims, 12 Drawing Sheets

Related U.S. Application Data

(60) Provisional application No. 61/023,674, filed on Jan. 25, 2008.

(51) Int. Cl.
  *G06F 17/50* (2006.01)
  *C12Q 1/6816* (2018.01)
  *G06F 19/18* (2011.01)

(58) Field of Classification Search
  USPC .................................................. 702/85, 99
  See application file for complete search history.

(56) References Cited

U.S. PATENT DOCUMENTS

| | | | | |
|---|---|---|---|---|
| 8,412,466 | B2 * | 4/2013 | Kanderian | C12Q 1/6827 435/6.1 |
| 9,133,504 | B2 * | 9/2015 | Hassibi | C12Q 1/6818 |
| 2004/0005595 | A1 * | 1/2004 | Browne | C07H 21/04 506/9 |
| 2004/0110219 | A1 | 6/2004 | Buchholz et al. | |
| 2004/0247694 | A1 * | 12/2004 | Bogas Cardenosa | A61K 35/54 424/580 |
| 2006/0094108 | A1 | 5/2006 | Yoder et al. | |
| 2006/0129331 | A1 * | 6/2006 | Akilesh | G06F 19/20 702/20 |
| 2006/0177841 | A1 * | 8/2006 | Wangh | C12Q 1/6844 435/6.12 |
| 2006/0292619 | A1 * | 12/2006 | Carrick | C12Q 1/6851 435/6.18 |
| 2007/0026421 | A1 | 2/2007 | Sundberg et al. | |
| 2007/0154980 | A1 | 7/2007 | Gasper et al. | |
| 2008/0003649 | A1 | 1/2008 | Maltezos et al. | |
| 2008/0085839 | A1 * | 4/2008 | Klapproth | C12Q 1/6827 506/12 |
| 2009/0093375 | A1 * | 4/2009 | Arnold | C12Q 1/6825 506/12 |
| 2009/0204353 | A1 | 8/2009 | Cheng et al. | |
| 2009/0222503 | A1 * | 9/2009 | Palais | C12Q 1/6816 708/277 |
| 2012/0178077 | A1 * | 7/2012 | DeCastro | G01K 11/06 435/3 |

FOREIGN PATENT DOCUMENTS

| | | |
|---|---|---|
| WO | 2005/064012 | 7/2005 |
| WO | 2007/035806 | 3/2007 |
| WO | 2009/094658 | 7/2009 |

OTHER PUBLICATIONS

Rutledge et al., "Mathematics of quantitative kinetic PCR and the application of standard curves," 31 Nucleic Acids Research e93 (2003).*
Applied Biosystems, "Guide to Performing Relative Quantitation of Gene Expression Using Real-Time Quantitative PCR." (2004).*
Gundry et al., "Amplicon Melting analysis with Labeled Primers: A Closed Tube Method for Differentiating Homozygotes and Heterozygotes," 49:3 Clinical Chemistry 396-406 (2003).*
Wilhelm et al., "SoFAR: Software for Fully Automatic Evaluation of Real-Time PCR Data," 34 BioTechniques 324-332 (2003).*
Bio-Rad Laboratories, Inc., "Real-Time PCR Applications Guide," (2006).*
Roche Diagnostics GmbH, "PCR Applications Manual," (2006).*
M. Tevfik Dorak (Ed.), "Real-time PCR," School of Clinical Medical Sciences, Newcastle University (2006).*
Life Technolgies Corporation, "Real-time PCR handbook," (2012).*
Dorak (ed.), "Real-time PCR," Taylor and Francis, (2006).*
CYCLERTest, "Thermocycler Calibration Guide" (2011).*
Chinese Search Report for Application No. 200980110889.6 dated Dec. 5, 2012.
Al-Robaiy, S. et al., "Rapid Competitive PCR using Melting Curve Analysis for DNA Quantification", *Biotechniques, Informa Life Sciences Publishing*, vol. 31, No. 6, Dec. 1, 2001, 1382-1387.
Pals, G. et al., "A rapid and senstitive approach to mutation detection using real-time polymerase chain reaction and melting curve analyses, using BRCA1 as an example", *Molecular Diagnosis*, Naperville, IL, vol. 4, No. 3, Sep. 1, 1999, 241-246.
PCT/US2009/032049, International Preliminary Report on Patentability dated Aug. 5, 2010.
PCT/US2009/032049, International Search Report dated Jun. 3, 2009.
Sanchez, Aquiles, S. J. et al., "Linear After the Exponential (Late)—PCR: An advanced method of asymmetric PCR and its uses in quantitative real time analysis", *Proceedings of the National Academy of sciences of USA*, National Academy of Science, Washington D.C, vol. 101, No. 7, Feb. 17, 2004, 1933-1938.
Wittwer, C. T. et al., "Continous Fluorescence Monitoring of Rapid Cycle DNA Amplification", *Biotechniques*, Informa Life Sciences Publishing, Westborough, MA, vol 22, No. 1, Jan. 1, 1997, 130-138.
SANCHEZ, J.A. et al., "Linear-After-The-Exponential (LATE)—PCR: An advanced method of asymmetric PCR and its uses in quantitative real-time analysis", *PNAS*, vol. 101(7), Feb. 17, 2004, 1933-1938.

* cited by examiner

| | Sample Genotype ID | Uncorrected MCD(40%) | Corrected MCD(90%) | | Sample Genotype ID | Uncorrected MCD(40%) | Corrected MCD(90%) | | Sample Genotype ID | Uncorrected MCD(40%) | Corrected MCD(90%) |
|---|---|---|---|---|---|---|---|---|---|---|---|
| 1 | NTC | variant | variant | 33 | hom | hom | hom | 65 | hom | wt | hom |
| 2 | wt | wt | wt | 34 | wt | het | het | 66 | het | het | het |
| 3 | het | wt | het | 35 | het | het | het | 67 | het | het | het |
| 4 | het | wt | het | 36 | unknown | wt | wt | 68 | het | het | het |
| 5 | het | wt | het | 37 | wt | hom | wt | 69 | hom | wt | hom |
| 6 | wt | hom | wt | 38 | hom | wt | hom | 70 | hom | wt | hom |
| 7 | het | het | het | 39 | het | het | het | 71 | hom | wt | hom |
| 8 | wt | hom | wt | 40 | hom | wt | hom | 72 | hom | wt | hom |
| 9 | wt | hom | wt | 41 | het | het | het | 73 | hom | wt | het |
| 10 | hom | wt | hom | 42 | hom | hom | hom | 74 | het | wt | het |
| 11 | hom | wt | hom | 43 | het | het | het | 75 | hom | wt | variant |
| 12 | wt | wt | wt | 44 | het | het | het | 76 | het | het | het |
| 13 | het | wt | het | 45 | het | het | het | 77 | het | het | het |
| 14 | het | wt | het | 46 | het | het | het | 78 | het | hom | het |
| 15 | het | wt | het | 47 | het | het | het | 79 | wt | wt | wt |
| 16 | het | het | het | 48 | ntc | variant | variant | 80 | hom | wt | hom |
| 17 | het | wt | variant | 49 | hom | wt | het | 81 | het | het | het |
| 18 | hom | wt | hom | 50 | hom | wt | het | 82 | hom | wt | hom |
| 19 | hom | wt | het | 51 | het | het | het | 83 | hom | wt | hom |
| 20 | het | wt | het | 52 | hom | het | hom | 84 | het | variant | het |
| 21 | hom | het | het | 53 | het | het | het | 85 | hom | wt | hom |
| 22 | het | het | het | 54 | hom | het | hom | 86 | hom | wt | hom |
| 23 | het | wt | het | 55 | het | het | het | 87 | wt | wt | wt |
| 24 | het | wt | het | 56 | het | het | het | 88 | hom | wt | hom |
| 25 | het | wt | het | 57 | hom | wt | hom | 89 | hom | wt | hom |
| 26 | het | wt | het | 58 | hom | wt | hom | 90 | hom | wt | hom |
| 27 | het | wt | het | 59 | ntc | hom | variant | 91 | het | wt | hom |
| 28 | het | het | het | 60 | het | wt | het | 92 | het | wt | het |
| 29 | het | het | het | 61 | het | wt | het | 93 | het | wt | hom |
| 30 | wt | hom | wt | 62 | hom | wt | hom | 94 | hom | wt | hom |
| 31 | wt | hom | wt | 63 | hom | wt | hom | 95 | hom | wt | hom |
| 32 | het | het | het | 64 | het | het | het | 96 | ntc | variant | variant |

FIG. 10

| Sample ID | $T_m$ | Delta Max | $T_{DeltaMax}$ | Sum of Absolute Difference (SAD) |
|---|---|---|---|---|
| 1. Wild Type | 83.9 | 0.0 | N/A | 0.0 |
| 2. Het 5 | 84.1 | 18.5 | 82.1 | 555.8 |
| 3. Het 14 | 84.2 | 35.2 | 84.2 | 1113.4 |
| 4. Het 11 | 84.2 | 49.1 | 84.0 | 1524.4 |
| 5. Het 4 | 84.3 | 41.3 | 84.2 | 1119.9 |
| 6. Het 10 | 84.3 | 51.4 | 84.2 | 1482.7 |
| 7. Het 6 | 84.3 | 57.0 | 84.2 | 1686.2 |
| 8. Het 8 | 84.3 | 65.8 | 84.1 | 2294.5 |
| 9. Het 3 | 84.3 | 65.9 | 84.2 | 2045.6 |
| 10. Het 7 | 84.3 | 74.5 | 84.1 | 2444.2 |
| 11. Het 12 | 84.4 | 82.9 | 84.2 | 2537.8 |
| 12. Het 9 | 84.5 | 73.7 | 84.3 | 1782.6 |
| 13. Het 13 | 84.5 | 100.0 | 84.2 | 3260.9 |

FIG. 11

METHODS FOR THE ANALYSIS OF DISSOCIATION MELT CURVE DATA

CROSS-REFERENCE TO RELATED APPLICATIONS

This application is a continuation of U.S. application Ser. No. 12/359,241, filed Jan. 23, 2009, which claims priority to U.S. Provisional Application No. 61/023,674, filed Jan. 25, 2008, which disclosures are herein incorporated by reference in their entirety.

FIELD

The field of disclosure of relates to methods for analyzing melt curve data, especially as the analysis relates to data for which the melting temperatures of the plurality of samples varies by only a fraction of a degree.

BACKGROUND

DNA amplification methods provide a powerful and widely used tool for genomic analysis. Polymerase chain reaction (PCR) methods, for example, permit quantitative analysis to determine DNA copy number, sample source quantitation, and transcription analysis of gene expression. Melting curve analysis is an important tool used to discriminate real amplification products from artifacts, for genotyping, and for mutation scanning. DNA analysis methods allow the detection of single base changes in specific regions of the genome, such as single nucleotide polymorphisms (SNPs). SNP analysis and other techniques facilitate the identification of mutations associated with specific diseases and conditions, such as various cancers, thalassemia, or others.

Statistical assay variations in melt curve data result from system noise in an analysis system, such as the thermal non-uniformity of a thermocycler block in a thermal cycler apparatus. For certain genotyping applications, the melting point shift between samples may be only fractions of a degree. In the case of SNP analysis, the SNP mutations may shift the melting point temperature by no more than 0.2° C.

Accordingly, there is a need in the art for methods of analyzing small differences in melting curves in the presence of the inherent noise of the analysis.

BRIEF DESCRIPTION OF THE DRAWINGS

FIG. 10 is a set of experimental data that has been analyzed according to various embodiments of methods for the analysis of dissociation melt curve data.

FIG. 11 is a set of experimental data that has been analyzed according to various embodiments of methods for the analysis of dissociation melt curve data.

DETAILED DESCRIPTION

Figure 1:
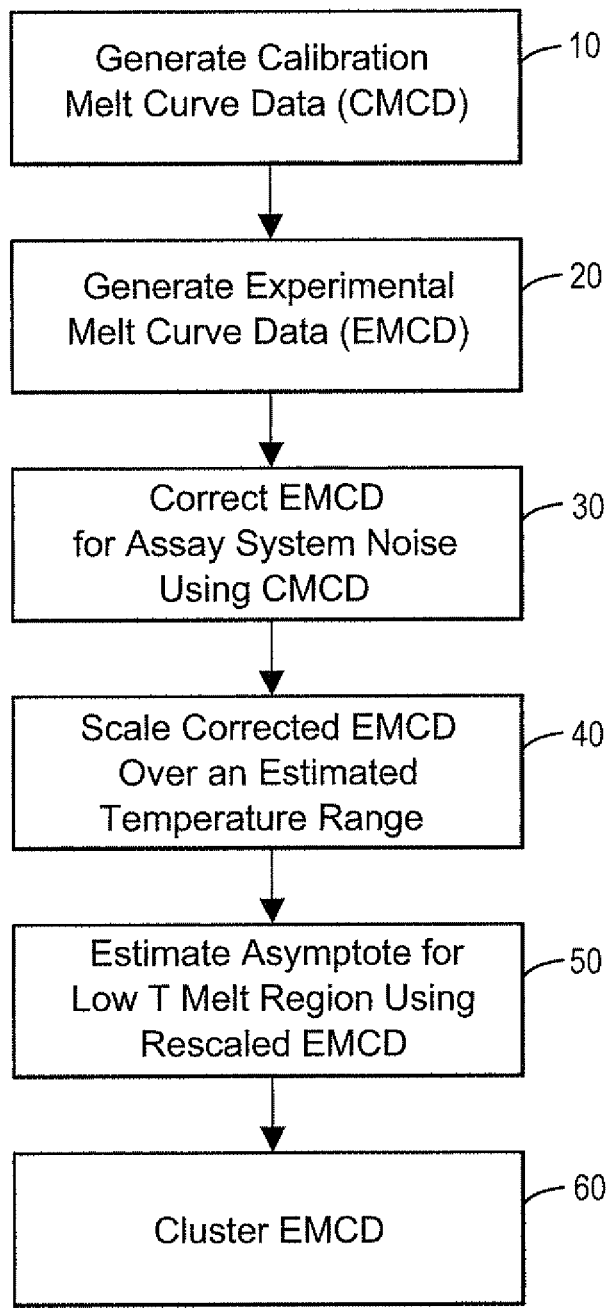
FIG. 1 is a flow chart that depicts various embodiments of methods for the analysis of dissociation melt curve data.

What is disclosed herein are various embodiments of methods for analyzing dissociation melt curve data, or as it is used throughout herein, melt curve data (MCD), where the differences in the melting points between various samples are small. For example, various embodiments of methods for analyzing dissociation melt curve data address samples sets where the differences in melting points may vary by only fractions of degrees. According to various embodiments of methods for the analysis of dissociation melt curve data, a calibration set of melt curve data may be used as a basis for correcting experimental sets of melt curve data, for example, with respect to assay system variance or noise. According to various embodiments, the melt curve data may be processed using curve-fitting techniques. In various embodiments of methods for analyzing dissociation melt curve data, different attributes of dissociation melt curve data, such those generated using a difference plot, may be used as the basis of cluster analysis of experimental melt curve data.

One known approach for DNA melting curve analysis utilizes fluorescence monitoring with intercalating double-strand-DNA specific dyes, such as for example, SYBR Green. The SYBR Green dye attaches to the DNA as double-stranded DNA amplification products are formed, and continues to bind to the DNA as long as the DNA remains double-stranded. When melting temperatures are reached, the denaturation or melting of the double-stranded DNA is indicated and can be observed by a significant reduction in fluorescence, as SYBR Green dissociates from the melted strand. The detected dye fluorescence intensity typically decreases about 1000-fold during the melting process. Plotting fluorescence as a function of temperature as the sample heats through the dissociation temperature produces a DNA melting curve. The shape and position of the DNA melting curve is a function of the DNA sequence, length, and GC/AT content.

Further, various approaches for validating the integrity of PCR reactions rely on melting curve analysis to discriminate artifact from real amplification product. Melting curve analysis can also be used to differentiate the various products of multiplexed DNA amplification, and to extend the dynamic range of quantitative PCR. DNA melting curve analysis is also used as a powerful tool for optimizing PCR thermal cycling conditions, because the point at which DNA fragments or other material melts and separate can be more accurately pinpointed.

In some embodiments, dissociation curve analysis methods calculate and display the first derivative of multi-component dye intensity data versus temperature, i.e., the differential melting curve. The melting temperature, $T_m$, at a peak of the differential melting curve can be used to characterize the product of a biochemical reaction. A sample with multiple amplification products will show multiple peaks in the differential melt curve. In some embodiments, melting curve detection involves very precise measurements of temperature and allows for the identification of a sample using the melting temperature, $T_m$. The determination of $T_m$ using various embodiments of methods for differential dissociation and melting curve detection is disclosed in related in U.S. patent application Ser. No. 12/020,369, which is incorporated herein by reference in its entirety.

Figure 3A:
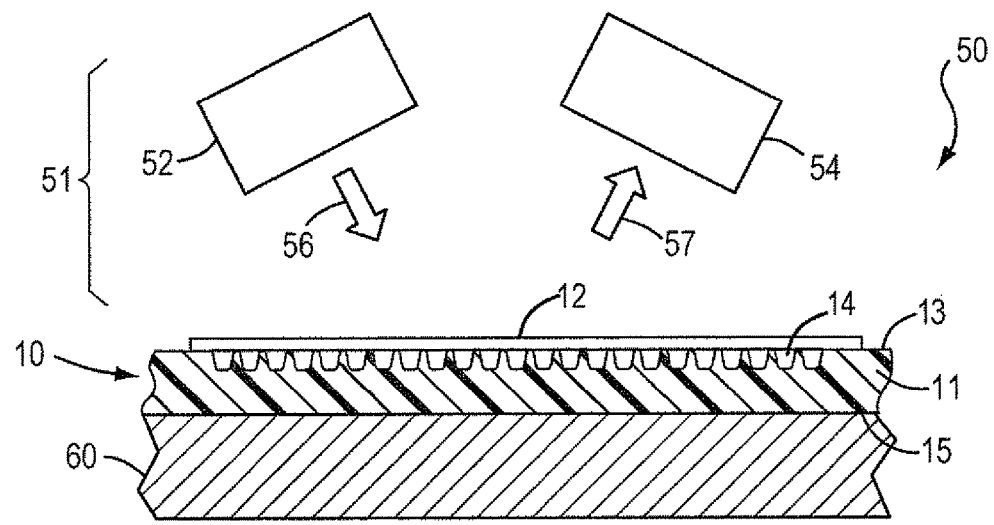
FIG. 3 depicts a series
Figure 3B:
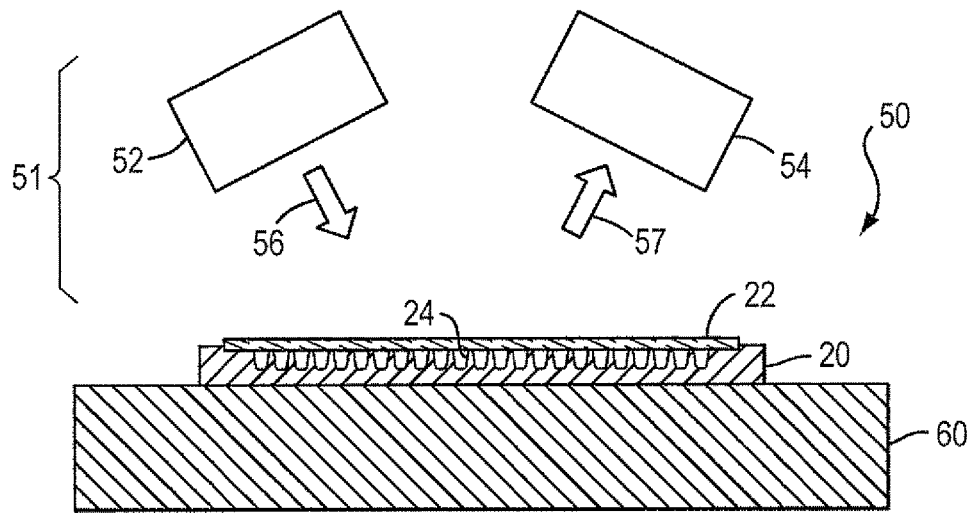

According to various embodiments as shown in FIG. 3A and FIG. 3B, a sample can be loaded into a sample support device. In various embodiments, as shown in FIG. 3A, a sample support device 10 comprises a substrate 11 having substantially planar upper and lower surfaces, 13, 15, respectively. Various embodiments of a sample support device may have a plurality of sample regions 14 on a surface 13. In various embodiments, the substrate 11 may be a glass or plastic slide with a plurality of sample regions 14, which may be isolated from the ambient by cover 12. Some examples of a sample support device may include, but are not limited by, a multi-well plate, such as a standard microtiter 96-well, a 384-well plate, or a microcard, as depicted in sample support device 20 of FIG. 3B, having a plurality of sample regions or wells 24, which may be isolated from ambient by cover 22. The sample regions in various embodiments of a sample support device may include depressions, indentations, ridges, and combinations thereof, patterned in regular or irregular arrays on the surface of the substrate. In FIG. 3A and FIG. 3B, a sample support device is shown placed in a thermal cycler system. In various embodiments of a thermal cycler system, there may be a heat block, 60, and a detection system 51. The detection system 51 may have an illumination source 52 that emits electromagnetic energy 56, and a detector 54, for receiving electromagnetic energy 57 from samples in sample support devices 10 and 20 in FIG. 3A and FIG. 3B, respectively.

In various embodiments, replicate aliquots of a sample can be loaded into the plate to determine the melting temperature, Tm, of the each well. Ideally, these temperatures should be identical throughout the wells, given that the samples are replicates. In practice, variations in the analysis system, for example, non-uniformity of heating elements of the analysis system, create variations in the set of replicates. According to various embodiments of methods for the analysis of dissociation melt curve data, such melt curve data using replicates may be used as a calibration set of data. In FIG. 1, step 10, such a plurality of melting points comprises a plurality or set of calibration melt curve data (CMCD). Similarly, as indicated in step 20 of FIG. 1, in a separate sample plate, unknown samples of interest for analysis may be dispensed into a plurality of support regions of a sample support device to determine the melting temperature of the unknown samples. Such a plurality of melting points comprises a plurality or set of experimental melt curve data (EMCD).

According to various embodiments of methods for the analysis of dissociation melt curve data, as depicted in step 30 of FIG. 1, signal processing steps may be applied to the raw dissociation melt curve data in advance of subsequent steps, such scaling, curve fitting, and cluster analysis. Such signal processing steps may include the correction of the EMCD with respect to assay system variance or noise. Sources of assay systems noise may include, for example, but not limited by, thermal non-uniformity, excitation source non-uniformity, and detection source noise.

According to various embodiments as indicated in FIG. 1 step 40, melt curve data may be processed to remove information that is not relevant for defining true differences among dissociation melt curves having melting temperatures that are different by only fractions of a degree, by scaling the data over an estimated temperature range.

Figure 4:
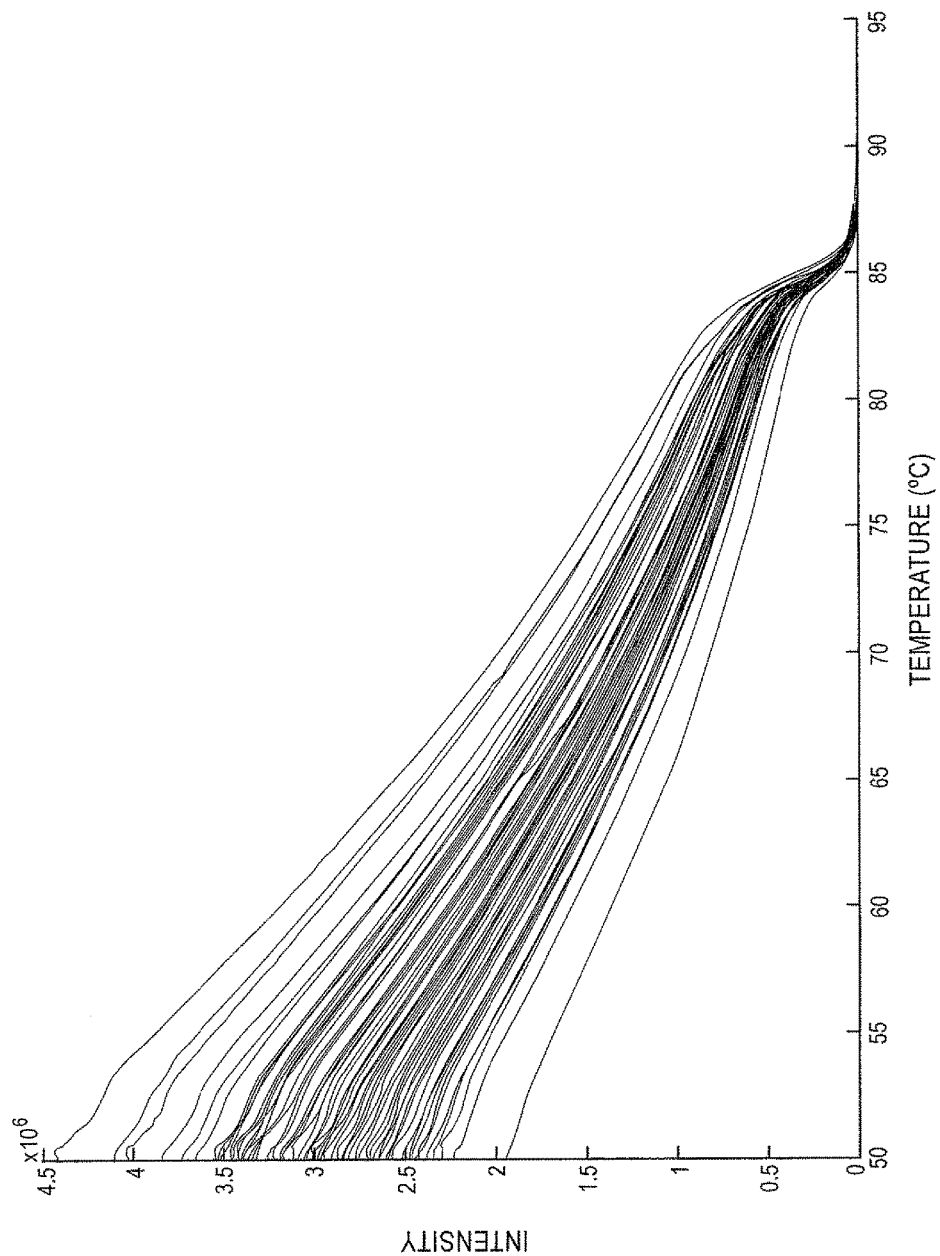
FIG. 4 depicts a series of dissociation melt curves for a set of calibration data.

For example, in FIG. 4, by using a set of CMCD, various embodiments of step 40 of FIG. 1 may be illustrated. The CMCD shown in FIG. 4 represents 96 replicates of a sample, where intensity of the signal is plotted as a function of temperature. Between 50° C. and 55° C., in the low temperature region of the curve, there are deviations from linearity that are artifacts, which are irrelevant to the melt curve data. Further, by inspecting FIG. 4, it is apparent that the melting occurs in a region of between about 70° C. to about 90° C., and that intensity approaches zero at temperatures above the melt. Additionally, the region from about 55° C. to about 80° C. a monotonic decrease in intensity is apparent. This is due to a decrease in the light emitted from the replicates as a result of the temperature dependence of dye emission, which is known to be an inverse relationship (i.e. dye emission decreases as temperature increases).

According to various embodiments of methods for the analysis of dissociation melt curve data as depicted in step 40 of FIG. 1, curve-fitting of the calibration data may be done based on the observations that the region between about 50° C. to about 55° C. contains artifacts, the region between 55° C. to about 80° C. should be linear, the melt occurs between about 70° C. to about 90° C., and the high temperature region above the melt approaches zero. In various embodiments, the curve-fitting of the calibration data may additionally use the information from a reference well in the calibration set. For example, a reference well may be selected as the initially brightest well in a calibration set before the melt curve analysis is run. A first derivative may be taken on the reference well melt curve data after the analysis is complete. The width of the first derivative peak of a reference well may be used in conjunction with the observation that the melting occurs in a region of between about 70° C. to about 90° C. to define the abscissa. Additionally, given that it is known that the region between 55° C. to about 80° C. should be linear, the ordinate may be scaled using a relative scale, wherein a maximum value of the ordinate scale is set by an intercept of the low temperature end of the melt curve data with the ordinate, and should approach zero at the high temperature range of the melt curve profile.

Figure 5:
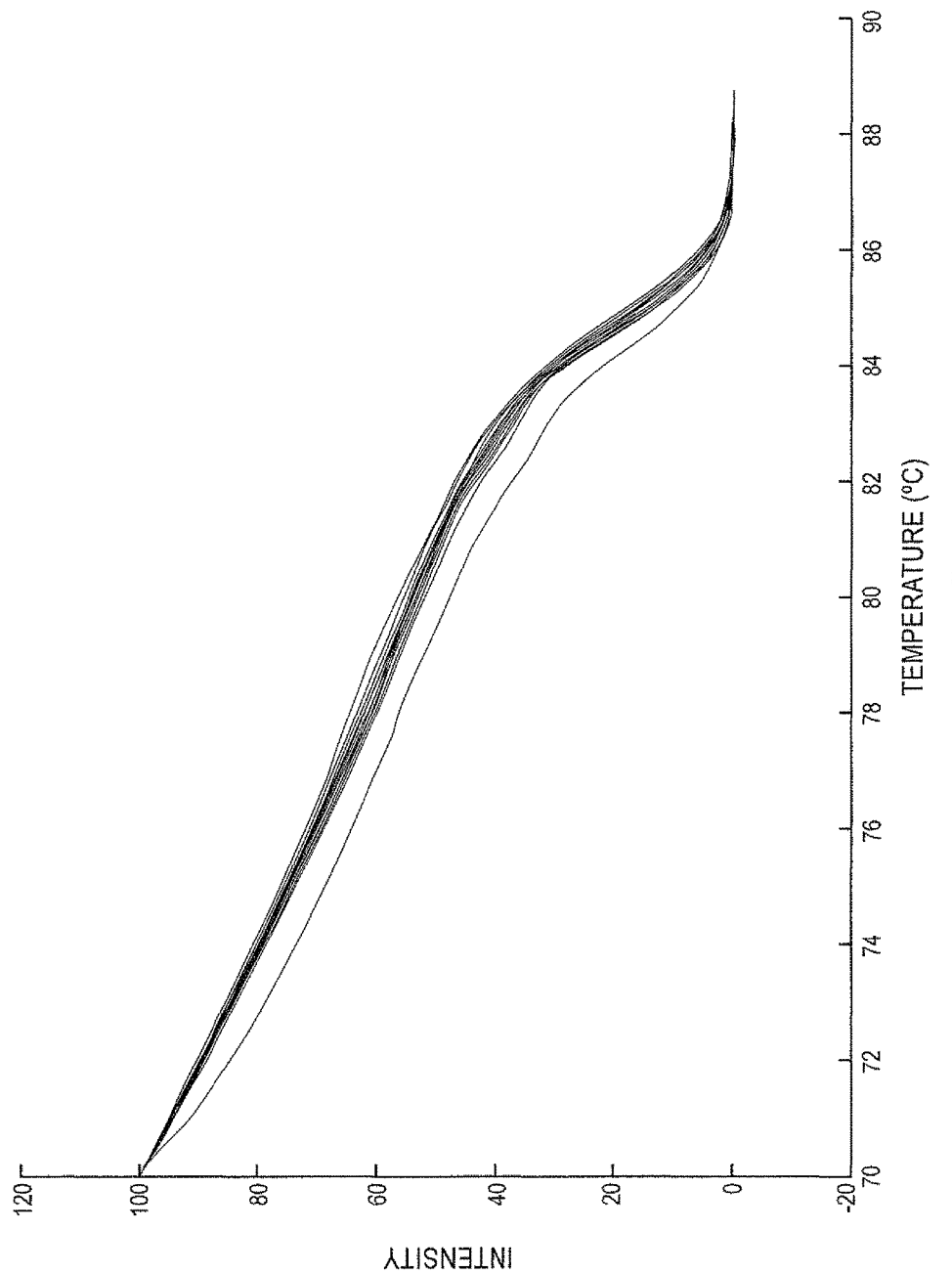
FIG. 5 depicts the series of graphs of FIG. 3 taken over an estimated temperature range according to various embodiments of methods for the analysis of dissociation melt curve data.

According to various embodiments of step 40 of FIG. 1, for the purpose of illustration, the CMCD of FIG. 4 has been scaled to produce the melt curve data shown in FIG. 5. For FIG. 5, the calibration data of FIG. 4 have been fit to an abscissa scaled to between about 70° C. to about 88° C. Additionally, the linear portion of the low melt end of the CMCD have been fit to 100 at intercept at the low temperature end of the scale, and approach zero at the high temperature range of the melt curve profile.

In various embodiments of methods for the analysis of dissociation melt curve data, in addition to the curve-fitting of step 40 of FIG. 1, additional curve-fitting steps maybe applied to the calibration data. For example, as indicated in step 50 of FIG. 1, according to various embodiments, it may be desirable to estimate an asymptote at the low temperature end of the curve for the purpose of detecting differences in data sets of melt curve data that have melting temperatures that vary by only fractions of a degree. Various embodiments for estimating an asymptote for the low temperature end of the melt curve data are depicted in FIGS. 6A and 6B.

Figure 6A:
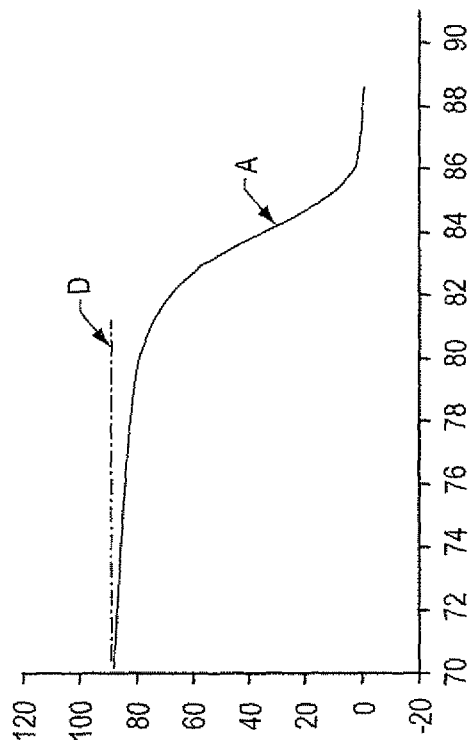
FIG. 6A and FIG. 6B illustrate estimating an asymptote according to various embodiments of methods for the analysis of dissociation melt curve data for the low temperature region of graphs, such as those shown in FIG. 5.
Figure 6B:
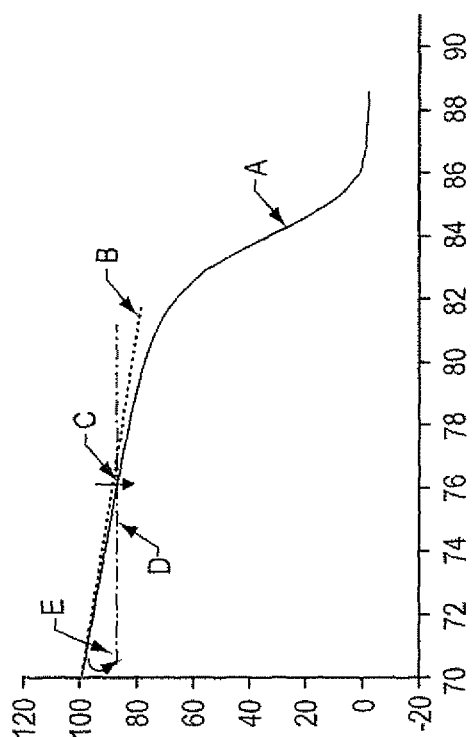

In FIG. 6A, line B may be extrapolated from a melt curve A by selecting a linear portion over a narrow region of the low temperature melt range. The linear portion may be selected, according to various embodiments, by an interval of a temperature change at a defined temperature point. According to various embodiments, the defined temperature point may be selected using the first derivative data, and defining a transition region, as for example, but not limited by, the full width at half the maximum of the first derivative peak. As one of ordinary skill in the art is apprised, such a transition region corresponds to an interval of two standard deviations about the midpoint of the first derivative curve. As such, other intervals about the curve may also be selected. In various embodiments, a temperature point may be selected at the low temperature end of the defined transition region, as the low temperature region is known to be linear. According to various embodiments, after a temperature point is selected, an interval from the point containing enough data points to extrapolate a line is selected. In that regard, the interval would correspond to at least two data points. According to various embodiments, the interval may be at least about 0.1° C. In various embodiments, the interval may be at least about 0.5° C. In still other embodiments, the interval may be at least about 1° C.

Figure 7:
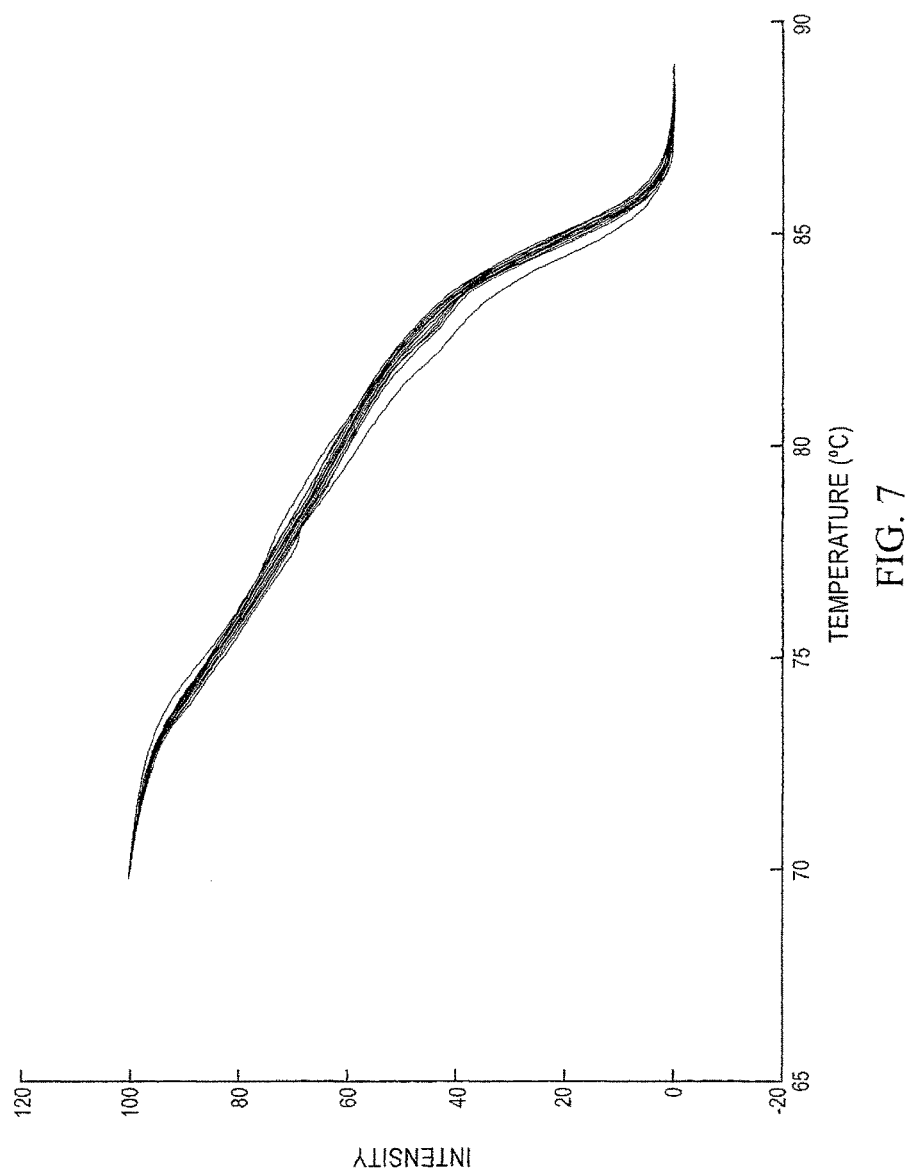
FIG. 7 depicts the series of graphs of FIG. 5 redrawn according to various embodiments of methods for the analysis of dissociation melt curve data shown in FIG. 6A and FIG. 6B.

For example a temperature point of about 70.0° C. may be selected, with an interval of plus or minus 0.5° C. around the temperature point. From this narrow linear region, a line, such as line B in FIG. 6A can be extrapolated. An algorithm, such as the subtraction of melt curve A and line B, can be used to evaluate a point where the two functions deviate by preset limit. For example, but not limited by, when the difference between the two curves is at least as great as, for example, twice the assay noise, then the calculated difference may indicate a significant difference. Alternatively, in various embodiments, other methods for determining a point where the two functions deviate by preset limit, such as the method for detecting nonlinearity in analog circuit analysis, may be used. Such a preset limit is designated as point C in FIG. 6A. Point C defines a point through which line D is drawn horizontally through the ordinate, thereby defining an estimated asymptote for the low temperature region. The calibration melt curve A is then fit accordingly to this asymptote, line D, as shown in FIG. 6B. In FIG. 7, the calibration data of FIG. 5 have been fit to an estimated low temperature asymptote.

Figure 8:
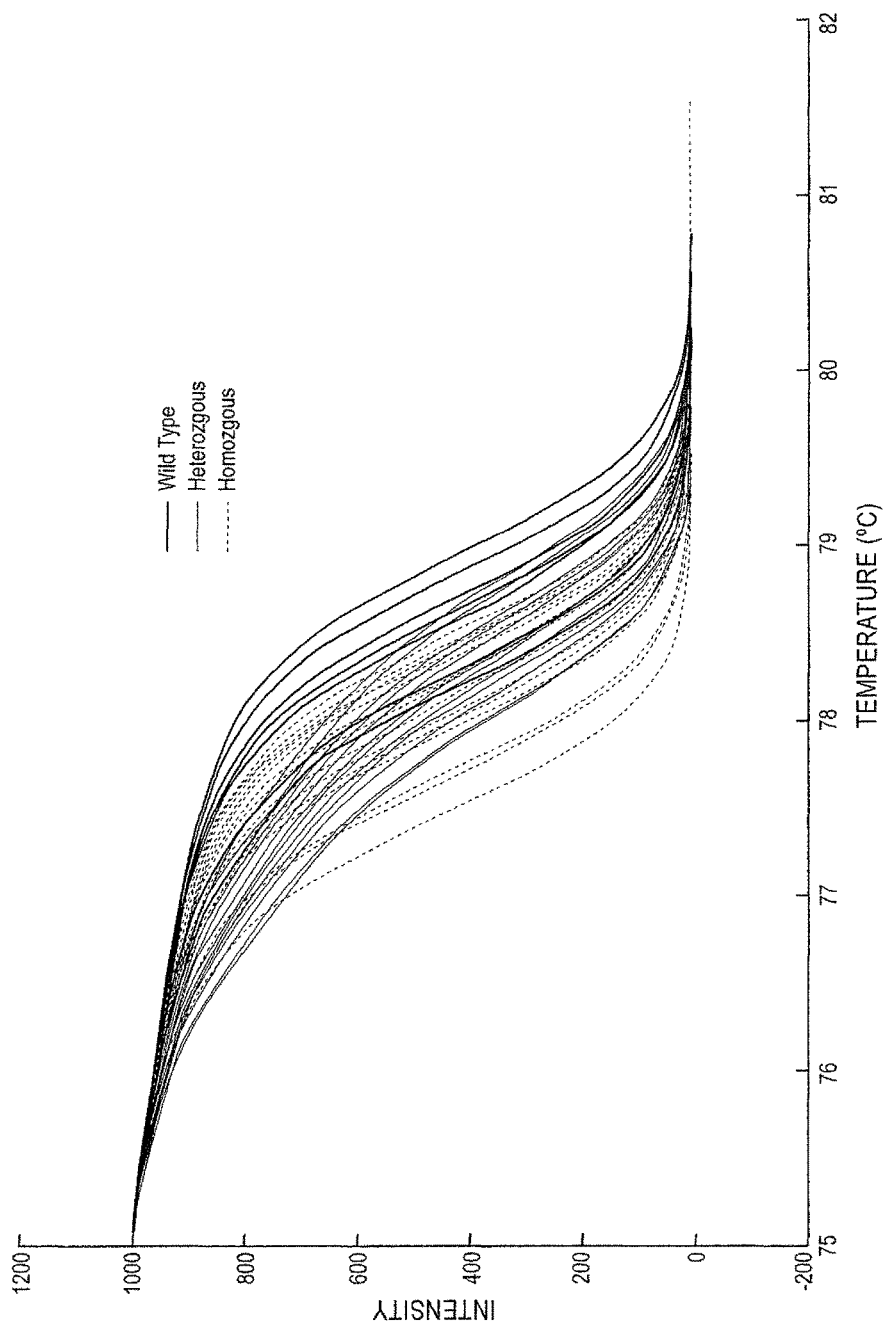
FIG. 8 depicts a series of dissociation melt curves for a set of experimental data according to various embodiments of methods for the analysis of dissociation melt curve data.

Step 40 and step 50 in FIG. 1 can be applied to a set of experimental data generated using test samples. The data presented in FIG. 8 represent a set of experimental data that have been fit according to various embodiments of methods described by step 40 and step 50 of FIG. 1. The EMCD in FIG. 8 have been clustered according genotype. In inspecting the EMCD of FIG. 8, there appears to be significant overlap of the melt curve data for the genotypes.

As previously mentioned, as depicted in step 30 of FIG. 1, according to various embodiments, signal processing steps may be applied to the raw dissociation melt curve data in advance of steps, such as steps 40 and 50 of FIG. 1. Such signal processing steps may include the correction of the EMCD with respect to assay system variance or noise, such as, but not limited by, assay system thermal non-uniformities inherent in thermal cycler systems.

As previously stated, the calibration melt curve data set is generated from replicates of the same sample dispensed in support regions of a sample support device, the variations in the calibration data are due to the inherent assay system noise. Accordingly, the information in the calibration melt curve data can be used to correct the experimental melt curve data for system noise. For example, a reference sample region in the EMCD may be selected. According to various embodiments, the frequency plot of the intensities of the sample regions, such as a well, in a sample support device may be determined, and a sample region within two standard deviations of the peak intensity of the EMCD may be selected as a reference sample region. In various embodiments, the reference sample region of the EMCD corresponding to the greatest intensity may be selected, however any sample region within two standard deviations would not be an outlier; i.e. either too dim or to bright, for the purpose of selecting a reference sample region, such as a well. According to various embodiments for correcting system noise as indicated in step 20 of FIG. 1, the corresponding sample region for the CMCD is then selected as a CMCD reference sample region, such as a well. In various embodiments, a difference from the CMDC reference sample region to any sample region on the sample support may be calculated for any point along the melt curve data, or any form of the melt curve data, such as, but not limited by, derivative data. This correction of the variation of the sample support regions over the sample support device due to assay system noise may then be applied to the EMCD. Other types of approaches may be used to determine a correction factor. For example, an average of the intensities of the CMCD may be taken over the entire CMCD sample set. For any specific sample region of the CMCD, a correction may be determined by subtracting the sample region intensity from the average. That correction may then be applied to the corresponding sample region of the EMCD.

Figure 9:
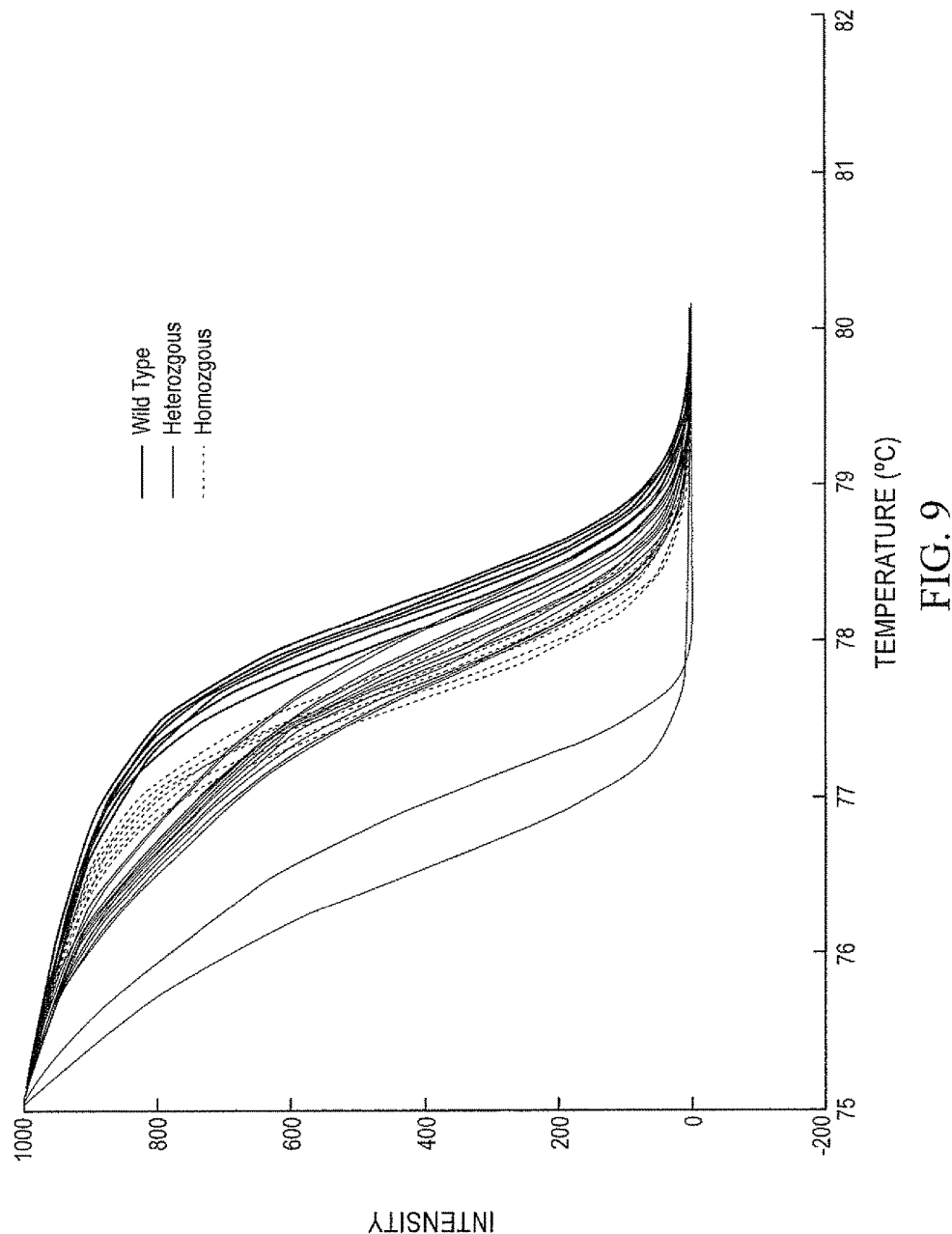
FIG. 9 depicts the series of graphs of FIG. 8 which have been corrected for assay system variance or noise according to various embodiments of methods for the analysis of dissociation melt curve data.

A correction as described above for step 20 of FIG. 1 was applied to FIG. 8, and the result is demonstrated in FIG. 9. It is apparent that the correction of the experimental data as displayed in FIG. 9 results in the ready clustering of the genotypes. A set of EMCD shown in tabular form is presented in FIG. 10. In FIG. 10, the first column displays the previously verified genotype of the samples. The second column represents the call made based on experimental data that was not corrected for assay system noise using calibration data. Finally, the third column represents the call made based on experimental data that was corrected for assay system noise using calibration data. As can be seen in the heading, the calls made using the uncorrected experimental data were correct 40% of the time, while the calls made using the corrected experimental data were correct 90% of the time. Moreover, the samples marked "ntc" are no-template controls, are negative controls for which no melt curve would be expected. The corrected MCD consistently assigns the negative controls correctly. Accordingly, various embodiments of methods for the analysis of dissociation melt curve data as depicted in FIG. 1 are effective in making determinations of genotyping, where the melting temperatures in an experimental set of data are different by only fractions of a degree.

Figure 12:
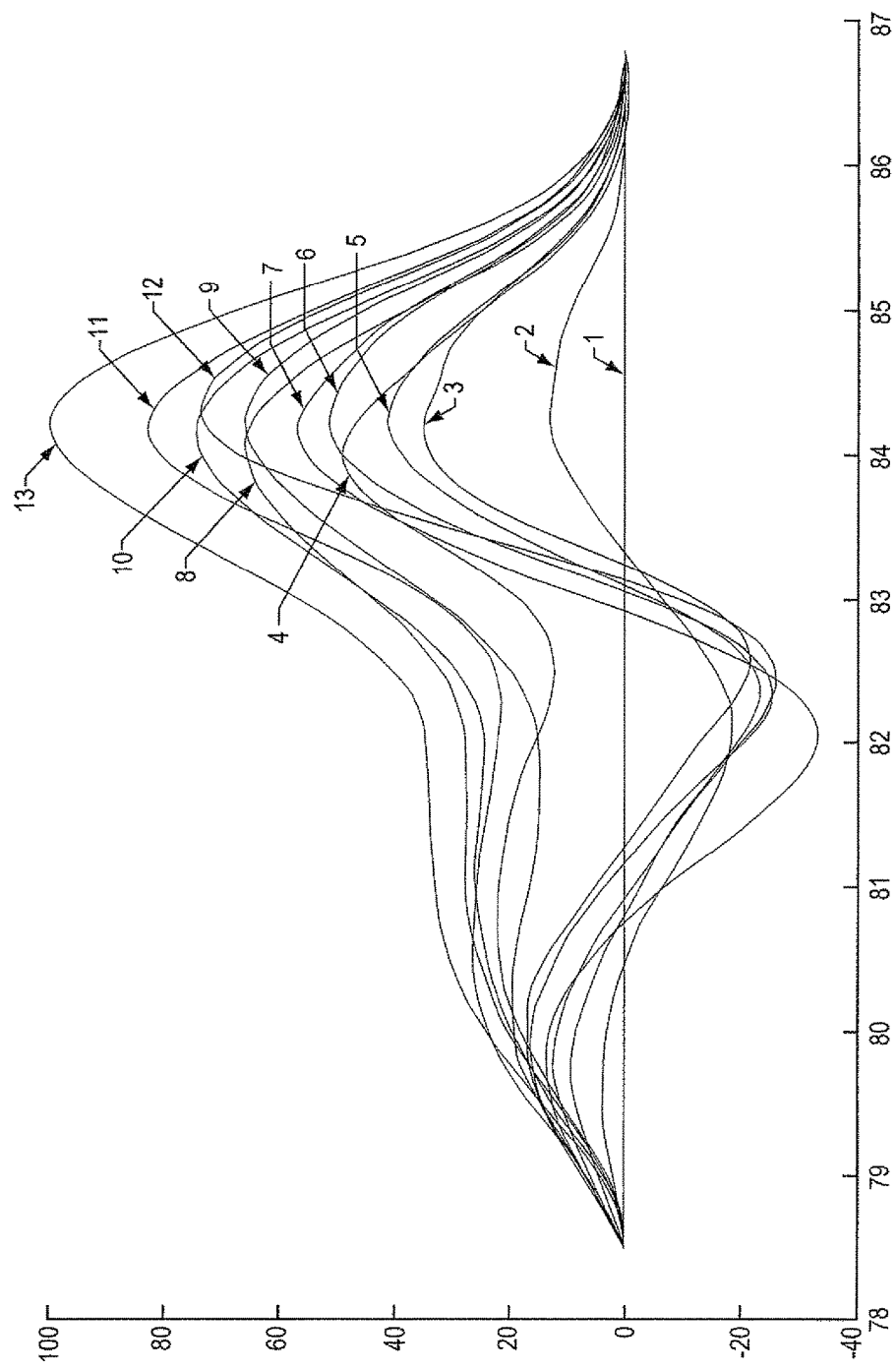
FIG. 12 is a graphical form of the experimental data of FIG. 11.

According to various embodiments of methods for the analysis of dissociation melt curve data, the experimental melt curve data can be further analyzed to detect true differences in data that are different by only fraction of a degree. According to various embodiments, in step 150 of FIG. 2, difference data may be generated using the experimental data. A plot of difference data for a set of experimental data is displayed in FIG. 12, and the corresponding samples are shown in the table of FIG. 11. In FIG. 12, the melt curve data for the wild type sample is taken as the data from which all other melt curve data for all other samples will be compared. The differences are taken between the melt curve data, and the wild type, and plotted in FIG. 12.

The scale on the abscissa is set as previously described. The ordinate scale is a relative scale based on the reference melt curve data defined as zero, by definition, and the minimum and maximum values set by greatest magnitude offset in the difference data. The data of interest corresponds to the attributes of the peaks in the positive region of the scale. The difference plots in FIG. 12 are labeled with respect to the corresponding samples listed in the table of FIG. 11.

In the table of FIG. 11, the melting temperature, $T_m$, is shown in the first column for the samples. In the second column, designated Delta Max, the values entered in that column refer to the value on the relative scale of the difference between the wild type and a sample peak, for the peaks in the positive region of the scale. In the third column, $T_{DeltaMax}$ is the corresponding temperature at Delta Max. In the last column, the sum of the absolute difference (SAD) is the area under the sample peak. Therefore, various embodiments of step 150 of FIG. 2 are demonstrated in FIG. 11 and FIG. 12, in which the creation of difference data, as shown in the plots of FIG. 12, becomes the basis of generating feature vectors in addition to the melting temperatures, such as Delta Max, $T_{DeltaMax}$, and SAD.

Figure 2:
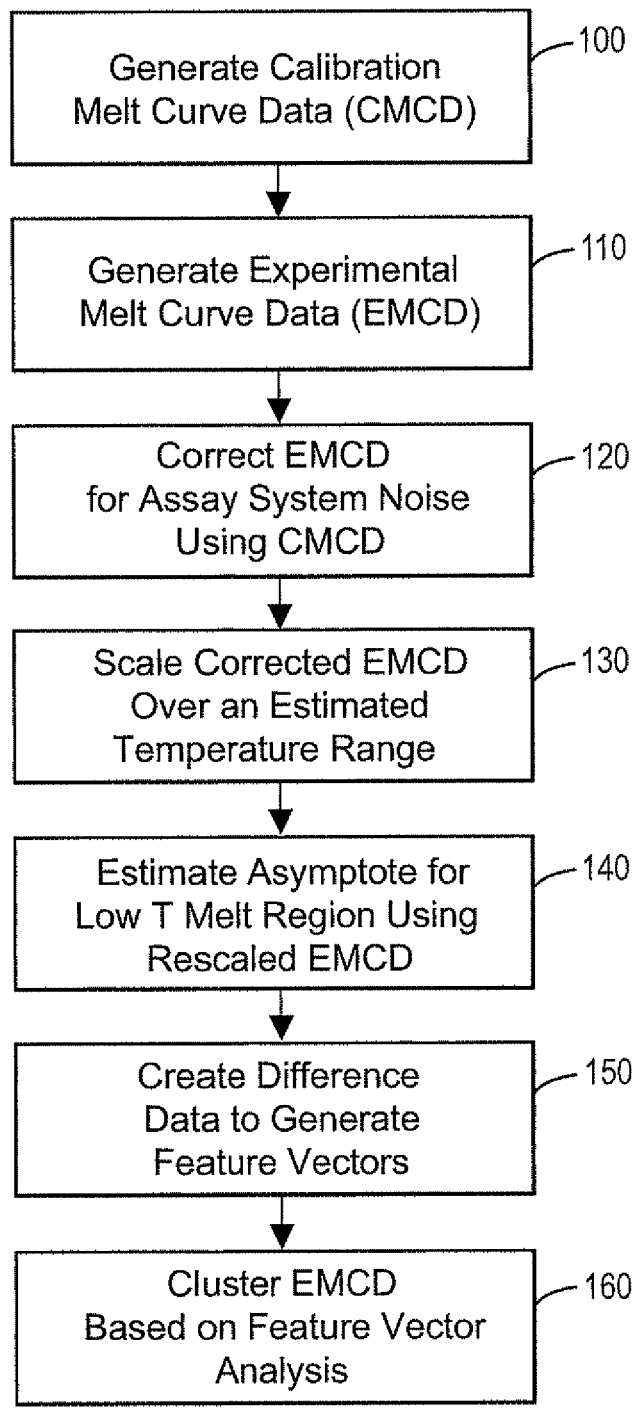
FIG. 2 is a flow chart that depicts various embodiments of methods for the analysis of dissociation melt curve data.

According to various embodiments of methods for the analysis of dissociation melt curve data as indicated by step 160 of FIG. 2, the feature vectors can be used to further discriminate differences in a set of data, where the melting temperatures are different by only a fraction of a degree. For example, in the table of FIG. 11, the samples are known to be samples that should not be clustered. That is, unlike the data represented in FIG. 9, for which there were multiple samples, or clusters of samples, for a genotype, for the data represented in FIG. 11, the samples should be distinct. Using the features vectors provides more information for which samples having melting temperatures that are different by only a fraction of a degree may be further discriminated. Through the inspection of the data in the table of FIG. 11, it is apparent that sample 2, having a $T_m$ of 84.1° C. is different from samples 3 and 4, which have the same $T_m$ of 84.2° C., by only 0.1° C. However, the Delta Max for the three samples is strikingly different, and clearly differentiates them. In this regard, the use of an additional feature vector may be used to further discriminate the samples.

Likewise, the block of data indicated with hatching; samples 5-10, all have melting temperatures of 84.5° C. Though most of the samples may be further discriminated by using Delta Max, samples 8 and 9 are only distinguished using the SAD feature vector. According to various embodiments of methods for the analysis of dissociation melt curve data in step 160 of FIG. 2, some or any combination of the feature vectors may be used to further evaluate EMCD. In various embodiments of step 160 of FIG. 2, the EMCD may be sorted by feature vectors sequentially, and an evaluation of fit may be made at after each iteration. According to various embodiments of step 160 of FIG. 2, the EMCD may be sorted by one feature vector or any combination of feature vectors as an iterative process, and an evaluation of the data may be evaluation of fit may be made after each iteration While the principles of this invention have been described in connection with specific embodiments of methods for analyzing dissociation melt curve data, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

What is claimed is:

1. A method of a biological analysis system for analyzing melt curve data, wherein the biological analysis system includes a processor and a display, the method comprising:
generating, by the processor, a calibration set of melt curve data for a calibration nucleic acid sample, wherein the calibration set is generated from subjecting the calibration nucleic acid sample deposited in a first plurality of support regions to conditions sufficient to denature nucleic acid replicates in the calibration nucleic acid sample;
generating, by the processor, an experimental set of melt curve data for at least one test nucleic acid sample, wherein the experimental set is generated from subjecting the at least one test nucleic acid sample deposited in a second plurality of support regions to conditions sufficient to denature nucleic acids in the at least one test nucleic acid sample;
correcting, by the processor, assay system noise in the experimental set of melt curve data using the calibration set of melt curve data, wherein the assay system noise is caused by at least thermal non-uniformity between support regions from the first plurality of support regions and the second plurality of support regions, and wherein correcting the experimental set of melt curve data for assay system noise using the calibration set of melt curve data further comprises:
calculating, for the calibration set of melt curve data, a correction value comprising a difference between data from at least two support regions among the first plurality of support regions in which the calibration nucleic acid sample is deposited, and
applying, for the experimental set of melt curve data, the calculated correction value to data from at least one of the second plurality of support regions in which the at least one test nucleic acid sample is deposited;
scaling the corrected experimental set of melt curve data over an estimated temperature range;
fitting the scaled corrected experimental set of melt curve data to an estimated asymptote for a low temperature region of a melting region of the melt curve data;
clustering the experimental set of melt curve data based on the steps of correcting, scaling and fitting; and
displaying, on the display, the corrected experimental set of melt curve data to a user.

2. The method of claim 1, wherein the method further comprises creating difference data from the experimental melt curve data for a plurality of nucleic acid samples, wherein the experimental melt curve data for one of the plurality of nucleic acid samples is selected as a reference, and the experimental melt curve data for the remaining nucleic acid samples are subtracted from the reference nucleic acid sample to create the difference melt curve data.

3. The method of claim 2, wherein feature vectors for one or more of the plurality of samples are generated from the difference melt curve data.

4. The method of claim 2, further comprising genotyping the plurality of nucleic acid samples based on the generated difference melt curve data.

5. The method of claim 3, wherein clustering the experimental set of melt curve data further comprises:
clustering the experimental melt curve data based on the difference melt curve data.

6. The method of claim 3, wherein the feature vector for at least one sample from among the plurality of nucleic acid samples comprises one or more of a delta max, a melt temperature at delta max, and a sum of an absolute difference, wherein the delta max comprises a difference between a peak value for the at least one nucleic acid sample and the reference nucleic acid sample, the melt temperature at delta max comprises the melt temperature at the peak value, and the sum of the absolute difference comprises the area under the sample peak.

7. The method of claim 1, wherein the correcting is based on a derivative form of the experimental melt curve data.

8. The method of claim 1, wherein the calibration set of melt curve data is generated based on detected changes to an indicator exhibited by the plurality of support regions in which the calibration nucleic acid sample is deposited, the detected changes occurring during the subjecting to conditions sufficient to denature the nucleic acid replicates in the calibration nucleic acid sample.

9. A biological analysis system for analyzing melt curve data, the biological analysis system comprising:
a processor configured to:
generate a calibration set of melt curve data for a calibration nucleic acid sample, wherein the calibration set is generated from subjecting the calibration nucleic acid sample deposited in a first plurality of support regions to conditions sufficient to denature nucleic acid replicates in the calibration nucleic acid sample;
generate an experimental set of melt curve data for at least one test nucleic acid sample, wherein the experimental set is generated from subjecting the at least one test nucleic acid sample deposited in a second plurality of support regions to conditions sufficient to denature nucleic acids in the at least one test nucleic acid sample;
correct assay system noise in the experimental set of melt curve data using the calibration set of melt curve data, wherein the assay system noise is caused by at least thermal non-uniformity between support regions from the first plurality of support regions and the second plurality of support regions, and wherein correcting the experimental set of melt curve data for assay system noise using the calibration set of melt curve data further comprises:
calculating, for the calibration set of melt curve data, a correction value comprising a difference between data from at least two support regions among the first plurality of support regions in which the calibration nucleic acid sample is deposited, and
applying, for the experimental set of melt curve data, the calculated correction value to data from at least one of the second plurality of support regions in which the at least one test nucleic acid sample is deposited;
scale the corrected experimental set of melt curve data over an estimated temperature range;
fit the scaled corrected experimental set of melt curve data to an estimated asymptote for a low temperature region of a melting region of the melt curve data;
cluster the experimental set of melt curve data based on the steps of correcting, scaling and fitting; and
a display configured to:
display the corrected experimental set of melt curve data to a user.

10. The biological analysis system of claim 9, wherein the processor is further configured to create difference melt curve data from the experimental melt curve data for a plurality of nucleic acid samples, wherein the experimental melt curve data for one of the plurality of nucleic acid samples is selected as a reference, and the experimental melt curve data for the remaining nucleic acid samples are subtracted from the reference nucleic acid sample to create the difference melt curve data.

11. The biological analysis system of claim 10, wherein feature vectors are generated from the difference melt curve data.

12. The system of claim 10, wherein the processor is configured to genotype the plurality of nucleic acid samples based on the generated difference melt curve data.

13. The biological analysis system of claim 11, wherein clustering the experimental set of melt curve data comprises:
clustering the experimental melt curve data based on the difference melt curve data.

14. The system of claim 11, wherein the feature vector for at least one sample from among the plurality of nucleic acid samples comprises one or more of a delta max, a melt temperature at delta max, and a sum of an absolute difference, wherein the delta max comprises a difference between a peak value for the at least one nucleic acid sample and the reference nucleic acid sample, the melt temperature at delta max comprises the melt temperature at the peak value, and the sum of the absolute difference comprises the area under the sample peak.

15. The biological analysis system of claim 9, wherein the processor is configured to correct the experimental set of melt curve data for assay system noise using a derivative form of the experimental melt curve data.

16. The system of claim 9, wherein the calibration set of melt curve data is generated based on detected changes to an indicator exhibited by the plurality of support regions in which the calibration nucleic acid sample is deposited, the detected changes occurring during the subjecting to conditions sufficient to denature the nucleic acid replicates in the calibration nucleic acid sample.

17. A method of a biological analysis system for analyzing melt curve data, wherein the biological analysis system includes a processor and a display, the method comprising:
generating a calibration set of melt curve data for a calibration nucleic acid sample, wherein the calibration set of melt curve data comprises fluorescence measurements collected by subjecting the calibration nucleic acid sample deposited in a first plurality of support regions to conditions sufficient to denature nucleic acid replicates in the calibration nucleic acid sample;
generating an experimental set of melt curve data for at least one test nucleic acid sample, wherein the experimental set of melt curve data comprises fluorescence measurements collected by subjecting the at least one test nucleic acid sample deposited in a second plurality of support regions to conditions sufficient to denature nucleic acids in the at least one test nucleic acid sample;
correcting assay system noise in the experimental set of melt curve data using a correction value calculated from the calibration set of melt curve data, wherein the assay system noise is caused by at least thermal non-uniformity between support regions from the first plurality of support regions and the second plurality of support regions;

scaling the corrected experimental set of melt curve data over an estimated temperature range;

fitting the scaled experimental set of melt curve data to an estimated asymptote for a low temperature region of a melting region of the melt curve data;

clustering the experimental set of melt curve data based on the steps of correcting, scaling and fitting; and displaying, on the display, the corrected experimental set of melt curve data to a user.

18. The method of claim 17, wherein correcting the experimental set of melt curve data comprises:

calculating, for the calibration set of melt curve data, the correction value, the correction value comprising a difference between data from at least two support regions from among the first plurality of support regions in which the calibration nucleic acid sample is deposited; and applying, for the experimental set of melt curve data, the calculated correction value to data from at least one of the second plurality of support regions in which the at least one test nucleic acid sample is deposited.

* * * * *